US006491923B1

(12) United States Patent
Davé et al.

(10) Patent No.: US 6,491,923 B1
(45) Date of Patent: Dec. 10, 2002

(54) STABILIZED CONJUGATES OF UNCOMPLEXED SUBUNITS OF MULTIMERIC PROTEINS

(75) Inventors: Kirti I. Davé, Thousand Oaks, CA (US); Janos Botyanszki, Camarillo, CA (US); Eva Sintar, Oxnard, CA (US)

(73) Assignee: Ivan E. Modrovich, Camarillo, CA (US)

( * ) Notice: Subject to any disclaimer, the term of this patent is extended or adjusted under 35 U.S.C. 154(b) by 0 days.

(21) Appl. No.: 09/565,286

(22) Filed: May 2, 2000

Related U.S. Application Data (60) Division of application No. 08/950,925, filed on Oct. 15, 1997, now Pat. No. 6,072,040, which is a continuation-in-part of application No. 08/730,111, filed on Oct. 15, 1996, now abandoned.

(51) Int. Cl.[7] ........................ A61K 39/385; G01N 31/00
(52) U.S. Cl. ...................... 424/193.1; 514/970; 435/15; 530/412; 530/418; 530/421; 530/810; 530/875
(58) Field of Search ................................. 530/412, 418, 530/421, 810, 815, 841; 424/193.1, 194.1; 514/970; 436/15

(56) References Cited

U.S. PATENT DOCUMENTS

| | | |
|---|---|---|
| 4,002,531 A | 1/1977 | Royer |
| 4,496,689 A | 1/1985 | Mitra |
| 4,766,106 A | 8/1988 | Katre et al. |
| 4,806,524 A | 2/1989 | Kawaguchi et al. |
| 4,847,325 A | 7/1989 | Shadle et al. |
| 4,902,502 A | 2/1990 | Nitecki et al. |
| 4,970,156 A | 11/1990 | Avrameas et al. |
| 5,089,261 A | 2/1992 | Nitecki et al. |
| 5,206,344 A | 4/1993 | Katre et al. |
| 5,283,317 A | 2/1994 | Saifer et al. |
| 5,288,623 A | 2/1994 | Zenno et al. |
| 5,298,410 A | 3/1994 | Phillips et al. |
| 5,324,775 A | 6/1994 | Rhee et al. |
| 5,324,844 A | 6/1994 | Zalipsky |
| 5,349,001 A | 9/1994 | Greenwald et al. |
| 5,359,030 A | 10/1994 | Ekwuribe |
| 5,446,090 A | 8/1995 | Harris |
| 5,468,478 A | 11/1995 | Saifer et al. |
| 5,475,052 A | 12/1995 | Rhee et al. |
| 5,529,915 A | 6/1996 | Phillips et al. |
| 5,556,788 A | 9/1996 | Kwan et al. |

FOREIGN PATENT DOCUMENTS

| | | |
|---|---|---|
| CA | 2 130 280 | 2/1995 |
| EP | 394819 B1 | 4/1990 |
| EP | 0650053 A1 | 4/1995 |
| EP | 07525426 A2 | 1/1997 |
| GB | 2 275 774 | 9/1994 |
| WO | WO 94/27156 | 11/1994 |
| WO | WO 95/02612 | 1/1995 |
| WO | WO 96/10076 | 4/1996 |
| WO | WO 96/27661 | 9/1996 |

OTHER PUBLICATIONS

Abe et al., "Early assessment of reperfusion therapy using troponin T" *JACC* (1994) 23(6):1382–1389.

Abuchowski et al., "Alteration of immunological properties of bovine serum albumin by covalent attachment of polyethylene glycol" *J. Biol. Chem.* (1977) 252(11):3578–3581.

Abuchowski et al., "Cancer therapy with chemically modified enzymes. I. Antitumor properties of polyethylene glycol–asparaginase conjugates" *Cancer Biochem. Biophys.* (1984) 7:175–186.

Abuchowski et al., "Effect of covalent attachment of polyethylene glycol on immunogenicity and circulating life of bovine liver catalase" *J. Biol. Chem.* (1977) 252(11):3582–3586.

Adams et al., "Cardiac troponin I. A marker with high specificity for cardiac injury" *Circulation* (1993) 88:101–106.

Antman et al., "Evaluation of a rapid bedside assay for detection of serum cardiac troponin T" *JAMA* (1995) 273(16):1279–1282.

Apple et al., "Cardiac troponin, CK–MB and myoglobin for the early detection of acute myocardial infarction and monitoring of reperfusion following thrombolytic therapy" *Clin. Chim. Acta* (1995) 237:59–66.

Arakawa et al., "Protein–solvent interactions in pharmaceutical formulations" *Pharm. Res.* (1991) 8:285–291.

Armour et al., "Cloning and expression in *Escherichia coli* of the cDNA encoding human cardiac troponin I" *Gene* (1993) 131:287–292.

Baschong et al., "Reversible fixation for the study of morphology and macromolecular composition of fragile biological structures" *Euro. J. Cell Biol.* (1983) 32:1–6.

Beachamp et al., "A new procedure for the synthesis of polyethylene glycol–protein adducts; effects on function, receptor recognition, and clearance of superoxide dismutase, lactoferrin, and $\alpha_2$–macroglobulin" *Anal. Biochem.* (1983) 131:25–33.

Bodor et al., "Development of monoclonal antibodies for an assay of cardiac troponin–I and preliminary results in suspected cases of myocardial infarction" *Clin. Chem.* (1992) 38(11):2203–2214.

(List continued on next page.)

*Primary Examiner*—Padmashri Ponnaluri
(74) *Attorney, Agent, or Firm*—Morrison & Foerster LLP (57) ABSTRACT

The present invention provides methods for preparing, and compositions comprising, stabilized protein-polymer conjugates. More particularly, the present invention relates to the stabilization of individual subunits of multisubunit protein complexes by conjugation to polymers. Such conjugation acts to stabilize the individual subunit in its native conformation in liquid medium, which in turn acts to stabilize its biological activity.

7 Claims, 4 Drawing Sheets

OTHER PUBLICATIONS

Bodor et al., "Cardiac troponin T composition in normal and regeneration human skeletal muscle" *Clin. Chem.* (1997) 43(3):476–484.

Boyce, "Cardiac markers: Which ones are labs using?" *Clinical Laboratory News* (Oct. 1996).

Braun et al, "Discrepant results for cardiac troponin T and troponin I in chronic myppathy, depending on instrument and assay generation" *Clin. Chem.* (1996) 42(12):2039–2041.

Chesebro and Fuster, "Thrombosis in unstable angina" *New Eng. J. Med.* (1992) 327:192–194.

Combes et al., "Raman spectroscope study of the effect of polyethylene glycol on the dynamics of water. Application to thermal denaturation of enzymes" *Annals of the New York Academy of Sciences* (1995) 750:66–70.

Editorial (author unknown), "Troponin T and myocardial damage" *Lancet* (1991) 338:23–24.

Etievent et al., "Use of cardiac troponin I as a marker of perioperative myocardial ischemia" *Ann. Thorac. Surg.* (1995) 59:1192–1194.

Gerhardt and Ljungdahl, "Rational diagnostic strategy in diagnosis of ischemic myocardial injury. S–troponin T and S–CK MB (mass time series using individual baseline values" *Scan. J. Clin. Lab. Invest.* (1993) 53(supp. 215):47–59.

Gerhardt et al., "Troponin–T and CK MB (mass) in early diagnosis of ischemic myocardial injury. The Helsingborg Study, 1992" *Clin. Biochem.* (1993) 26:231–240.

Ghosh et al., "Domains of macrophage NO synthase have divergent roles in forming and stabilizing the active dimeric enzyme" *Biochem.* (1996) 35:1444–1449.

Gottschalk et al., "Chemically crosslinked lactate dehydrogenase: Stability and reconstitution after glutaraldehyde fixation" *Biotech. Applied Biochem.* (1987) 9:389–400.

Guest et al., "Rapid diagnosis of acute myocardial infarction" *Cardiology Clinics* (1995) 13:283–294.

Haider et al., "Cardiac troponin–I: A biochemical marker for cardiac cell necrosis" *Disease Markers* (1993) 11:205–215.

Hake et al., "Tropinin T—a reliable marker of perioperative myocardial infarction?" *Eur. J. Cardio–thorac Surg.* (1993) 7:628–633.

Hamm et al., "The prognostic value of serum troponin T in unstable angina" *New Eng. J. Med.* (1992) 327:146–150.

Hamm et al., "New biochemical markers for myocardial cell injury" *Current Science* (1995) pp. 355–360.

Hermanson, "Modification with synthetic polymers" *Bioconjugate Techniques* (1996) Ch. 15 pp. 605–619, Academic Press.

Hossein–Nia et al., "Troponin T as a non–invasive marker of cardiac allograft rejection" *Lancet* (1993) 341:838.

Jaenicke, "Stability and folding of ultrastable proteins: eye lens crystallins and enzymes from thermophiles" *Faseb J.* (1996) 10:84–92.

Katre et al., "Chemical modification of recombinant interleukin 2 by polyethylene glycol increases its potency in the murine Meth A sarcoma model" *Proc. Natl. Acad. Sci. USA* (1987) 84:1487–1491.

Katre et al., "Immunogenicity of recombinant Il–2 modified by covalent attachment of polyethylene glycol" *J. Immunol.* (1990) 144(1):209–213.

Katrukha et al., "Troponin complex for the preparation of Troponin I calibrators and standards" *Hytest*, Turku, Finland. (1 page total).

Katrukha et al., "Troponin I is released in bloodstream of patients with acute myocardial infarction not in free form but as complex" *Clin. Chem.* (1997) 43(8):1379–1385.

Katus et al., "Diagnostic efficiency of troponin T measurements in acute myocardial infarction" *Circulation* (1991) 83(3):902–912.

Katus et al., "Proteins of the troponin complex" *Laboratory Medicine* (1992) 23(5):311–317.

Keffer, "Myocardial markers of injury" *Clin. Chem.* (1996) 105(3):305–320.

Knauf et al., "Relationship of effective molecular size to systemic clearance in rats of recombinant interleukin–2 chemically modified with water–soluble polymers" *J. Biol. Chem.* (1988) 263:15064–15070.

Kondo et al., "Improvement of proteolytic resistance of immunoadsorbents by chemical modification with polyethylene glycol" *Biotechnol. & Bioeng.* (1989) 34:532–540.

Larue et al., "Cardiac–specific immunoenzymometric assay of troponin I in the early phase of acute myocardial infarction" *Clin. Chem.* (1993) 39:972–979.

Löfberg et al., "Myosin heavy–chain fragments and cardiac troponins in the serum in rhabdomyolysis" *Arch. Neurol.* (1995) 62:1210–1214.

Mach et al., "Rapid bedisde whole blood cardiospecific troponin T in immunoassay for the diagnosis of acute myocardial infarction" *Am. J. of Cardio.* (1995) 75:842–845.

Mainfroid et al., "Stabilization of human triosephosphate isomerase by improvement of the stability of individual α–helices in dimeric as well as monomeric forms of the protein" *Biochem.* (1996) 35:4110–4117.

Mair et al., "Cardiac tropinin T in the diagnosis of myocardial injury" *Critical Reviews in Clinical Laboratory Sciences* (1992) 29(1):31–57.

Mair et al., "Cardiac tropinin T in the diagnosis of heart contusion" *Lancet* (1995) 338:693.

Mair et al., "Cardiac troponin 1 release correlates with myocardial infarction size" *Eur. J. Clin. Chem. Clin. Biochem.* (1995) 33:869–872.

Mair et al., "Equivalent early sensitivities of myogloblin, creatine kinase MB mass, creatine kinase isoform ratios, and cardiac troponins I and T for cute myocardial infarction" *Clin. Chem.* (1995) 41:1266–1272.

Mair et al., "Rapid accurate diagnosis of acute myocardial infarction in patients with non–traumatic chest pain within 1 h of admission" *Coronary Artery Disease* (1995) 6:539–545.

Marsh and Danielson, "Determination of substrates using poly(ethylene glycol)–stabilized dehydrogenase enzymes by microlite perminute flow injection" *Analyst* (1995) 120:1091–1096.

Marshall et al., "Enzyme stabilization by covalent attachment of carbohydrate" *Archives of Biochem. & Biophys.* (1975) 167:777–779.

Marshall et al., "Preparation and characterization of a Dextran–Trypsin conjugate" *J. Biol. Chem.* (1976) 251:1081–1087.

Molecular Cloning: A Laboratory Manual, $2^{nd}$ ed., vol. 1–3, eds. Sambrook et al. Cold Spring Harbor Laboratory Press (1989) (A title page and table of contents are included herewith).

Morpurgo et al., "Covalent modification of mushroom tyrosinase with different amphiphic polymers for pharmaceutical and biocatalysis applications" *Appl. Chem. & Biotechnol.* (1996) 56:59–71.

Muller–Bardorff et al., "Improved troponin T ELISA specific for cardiac troponin T isoform: assay development and analytical and clinical validation" *Clin. Chem.* (1997) 43(3):458–466.

Ohman et al., "Cardiac troponin T levels for risk stratification in acute myocardial ischemia" *New Eng. J. Med.* (1996) 335(18):1333–1341.

Ohman, E.M., "Researcher gives troponin T assay the edge over troponin I assay in cardiac testing" *Diagnostics Intelligence* (1996) 8(12):6–7.

Olah et al., "A model structure of the muscle protein complex $4Ca^{2+}$ troponin C·troponin I derived from small–angle scattering data: Implications for regulation" *Biochem.* (1994) 33:12800–12806.

Pasta et al., "Circular dichroism and fluorescence of polyethylene glycol–subtilism in organic solvents" *FEBS* (1988) 236:329–332.

Rabon et al., "Glutaraldehyde crosslinking analysis of the C12E8 solubilized H,K–ATPase" *Biochim. Biophys. Acta* (1990) 1039:277–289.

Ravkilde et al, "Diagnostic performance and prognostic value of serum tropinin T in suspected acute myocardial infarction" *Scan. J. Clin. Lab. Invest.* (1993) 53:677–685.

Scher et al., "Stabilization of immobilized lectin columns by crosslinking with glutaraldehyde" *Anal. Biochem* (1989) 177:168–171.

Scopes Protein Purification: Principles and practice, $2^{nd}$ ed., Springer–Verlag, New York. (1987) (Title page and table of contents included herewith).

Talasz et al., "Size–branch occlusion during percutaneous transluminal coronary angioplasty" *Lancet* (1992) 339:1380–1381.

Townsend et al, "Human cardiac troponin T: Identification of fetal isoforms and assignment of the TNNT2 locus to chromosome 1q" *Genomics* (1994) 21(2):311–316.

Tsuji et al., "Monomer of the B subunit of heat–labile enterotoxin from enteroxin from enterotoxigenic *Escherichia coli* has little ability to bind to $GM_1$ ganalioside compared to its coligenoid" *Microbiol. Immunol.* (1995) 39(10):817–819.

Ushikubo et al., "Molecular characterization of mitochondrial trifunctional protein deficiency: Formation of the enzyme complex is important for stabilization of both α– and β–subunits" *Am. J. Hum. Genet.* (1996) 58:979–988.

Vallins et al, "Molecular cloning of human cardiac troponin I using polymerase chain reaction" *FEBS* (1990) 270:57–61.

Wilkinson and Grand, "Comparison of amino acid sequence of troponin I from different striated muscles" *Nature* (1978) 271:31–35.

Wong, "Application of chemical cross–linking to soluble proteins" *Chemistry of Protein Conjugation and Cross–Linking* CRC Press, Inc. (1991) Chapter 8, pp. 221–231.

Wu and Lane, "Metaanalysis in clinical chemistry: Validation of cardiac troponin T as a marker for ischemic heart disease" *Clin. Chem.* (1995) 41(8):1228–1233.

Zalipsky et al., "Evaluation of a new reagent for covalent attachment of polyethylene glycol to proteins" *Biotechnol. Appl. Biochem.* (1992) 15:100–114.

Stability of free cTnI at 37°C

Fig. 3B

Stability of cTnI-PEG Conjugate at 37°C

STABILIZED CONJUGATES OF UNCOMPLEXED SUBUNITS OF MULTIMERIC PROTEINS

RELATED APPLICATION

This application is a divisional of U.S. Ser. No. 08/950,925, filed Oct. 15, 1997; now U.S. Pat. No. 6,072,040, which is a continuation-in-part of U.S. Ser. No. 08/730,111, filed Oct. 15, 1996, now abandoned, the contents of which are hereby incorporated by reference into the present disclosure.

TECHNICAL FIELD

The present invention relates to the conjugation of uncomplexed subunits of multisubunit protein complexes with polymers to stabilize their conformation. More specifically, the present invention describes a method of stabilizing these individual subunits via covalent conjugation to a natural or synthetic polymer. The present invention also relates to stabilized conjugates of cardiac troponin I and stabilized conjugates of cardiac troponin T, and methods for their preparation.

BACKGROUND ART

Proteins are composed of long chains of amino acids. The structure of proteins can be considered on four different levels. The primary structure refers to the specific order of amino acids in the polymer chain. The secondary structure refers to the interactions among and between the amino acids in the chain to form such structures as $\alpha$ helices and $\beta$ pleated sheets. The tertiary structure refers to the three-dimensional structure of the protein, which is also referred to as a protein's conformation. The quaternary structure refers to the spatial arrangement of individual polypeptides or "subunits" of multisubunit proteins.

The native conformation of a protein is only marginally stable. Thus, many proteins which are removed from their native environment and purified undergo conformational changes which can cause a loss of biological activity, such as enzyme activity or antibody binding capacity. In particular, the individual (uncomplexed) subunits of multisubunit protein complexes may undergo dramatic conformational changes when separated from the other subunits of the complex and stored in a liquid medium.

It is often desirable to separate the individual subunits of a multisubunit protein complex, for example to study or exploit the biological activity of each individual subunit. However, this may not be possible if the individual subunits undergo conformational changes in their uncomplexed state that alter their biological activity. Accordingly, it is an object of the present invention to provide a method for stabilizing individual subunits of multisubunit protein complexes.

Troponin is an example of a multisubunit protein complex which consists of three individual subunits; troponin T, troponin C and troponin I. The troponin complex is involved in the calcium-sensitive switch that regulates the interaction of actin and myosin in striated muscles. Troponin T binds the troponin complex to tropomyosin, while troponin I is the inhibitory subunit of the complex. Whereas troponin C from skeletal muscle and cardiac muscle is identical, troponin I and T from these two sources exist as different isoforms, each having a different amino acid sequences and thus a unique structure. Thus, cardiac troponin I (cTnI) and cardiac troponin T (cTnT) are of particular interest as cardiospecific markers.

After myocardial infarction, cTnT levels increase and remain elevated for an extended period. However, it has been reported that in a variety of disease states, cTnT is also expressed in skeletal muscle, which contributes to a lack of cardiospecificity of this protein. Furthermore, uremia, a condition associated with cardiomyopathy, is associated with elevated cTnT. Thus, a lack of absolute cardiospecificity makes this marker less than optimal for use in the early diagnosis of acute myocardial infarction (AMI).

Cardiac TnI is also released after acute myocardial infarction. In contrast to cTnT, cTnI has never been found in a healthy population, which includes marathon runners, in people with skeletal disease, or in patients undergoing non-cardiac operations. Thus, cTnI is a more specific marker for the diagnosis of AMI than other serum proteins.

A variety of immunoassays have been developed that utilize antibodies that can distinguish between the three troponins, and also between their different isoforms. Monoclonal and polyclonal antibodies have been designed and used in immunoassays which can detect the cardiac-specific epitopes formed by the unique amino acid sequence of cTnI. See, for example PCT Patent Application No. WO 96/10076; European Patent No. 394,819 B1; and Adams et al., *Circulation* 88:101–106 (1993). Larue et al., (*Clin. Chem.* 39:972–979 (1993)) describe an immunoenzyme assay that is capable of detecting cTnI in the concentration range of 0.2 to 20 $\mu$g/L in 30 minutes.

Immunoassays have also been described which are specific for TnT. See, for example, Katus, et al., *Circulation*, 83(3): 902–912 (1991). An immunoassay for TnT is also commercially available from Boehringer Mannheim Corp., Indianapolis, Ind.

Most immunoassays are designed to determine the concentration of a given marker in a patient's serum by comparing immunoassay results with the patient's serum to those obtained with control reagents of known concentration. One limitation in the development of immunoassays for the troponins involves the instability of the troponins in their uncomplexed state. Accordingly, there is a need for stabilized compositions of cTnI and cTnT that can be stored for extended periods of time, while retaining antibody binding capacity for use as control reagents in cTnI and cTnT immunoassays.

Stabilization of proteins via covalent conjugation to various polymers has been described. See, for example, U.S. Pat. No. 4,902,502; U.S. Pat. No. 5,468,478; U.S. Pat. No. 4,806,524; Katre et al., *J. Immunol.* 144:209–213 (1990); Abuchowski et al., *J. Biol. Chem.* 252:3582–3586 (1977). The properties conferred on the conjugated protein have been cited as increased in vivo half life, increased stability in solution, increased solubility, decreased susceptibility to proteases and decreased immunogenicity and antigenicity. For example, Nitecki et al. (U.S. Pat. No. 5,089,261) describe conjugating interleukin-2 to polyethylene glycol (PEG) to reduce immunogenicity.

In addition to stabilization of proteins via covalent conjugations to polymers, it has also been demonstrated that synthetic polymers are capable of providing a stabilizing effect via ionic interaction with proteins. For example, Marsh and Danielson (*Analyst* 120:1091–1096 (1995)) have described that the addition of PEG to an aqueous solutions of the multisubunit enzyme lactate dehydrogenase enhances the ability of the enzyme subunits to remain complexed.

The present invention relates to the finding that covalent conjugation of individual protein subunits of multisubunit proteins to polymers stabilizes the protein subunit, i.e. it maintains its native conformation in a liquid medium for a longer period of time than the equivalent unconjugated individual subunit. In a preferred embodiment, the present invention also relates to cTnI-polymer conjugates and cTnT-polymer conjugates which exhibit stabilized antibody binding capacity.

DISCLOSURE OF THE INVENTION

The present invention concerns stabilization of individual subunits of multisubunit protein complexes. Stabilization is accomplished by conjugating the individual subunits to a polymer. The stabilizing effect of conjugation allows the individual subunit to be stored in liquid medium for longer periods of time than an equivalent unconjugated or "free" individual subunit. This greatly enhances the shelf life of the composition. In a preferred embodiment, the stabilized individual subunits are either cTnI or cTnT, which in their unconjugated form are highly unstable in liquid medium.

Polymers which are useful in the present invention can be naturally occurring or synthetic. Whereas certain synthetic polymers may be preferred for stabilization of free cTnI, as will be discussed below, natural polymers such as serum proteins are preferred for stabilization of cTnT. A particularly preferred class of synthetic polymer is PEG. Other suitable polymers include, but are not limited to polyalkylene glycols, polyoxyethylated polyols, polyvinylpyrrolidone, polyhydroxyethyl methacrylate, polyvinyl alcohols, and polyurethane.

The polymers which are useful in the present invention may vary in molecular weight, and must have a molecular weight which is sufficient to stabilize the individual subunit. This generally requires that the polymer have a molecular weight between 100 and 200,000, more preferably between 1,000 and 40,000, and most preferably between 2,500 and 10,000.

In order to conjugate the polymer to the individual protein subunit, it should be in an "active" form, which means it must contain at least one reactive group capable of reacting with pendant groups on the protein to form a covalent linkage. When the polymer is PEG, a preferred active form is monomethoxy-PEG p-nitrophenyl carbonate.

The ratio of individual subunit to polymer in the conjugation reaction must be sufficient to stabilize the individual subunit. This generally requires that the polymer is provided in a molar concentration which is at least equivalent to the molar concentration of the individual subunit. Preferably, the polymer is provided in excess to ensure that a sufficient number of polymers are covalently attached to the individual subunits.

As an alternative to polymers, monomers (at least some of which are in an active form) can be used to form the protein-polymer conjugates of the present invention, which may polymerize during conjugation and may even attach directly to the protein subunit to afford the desired stability.

Another aspect of the present invention relates to compositions that consist of individual subunit-polymer conjugates in liquid medium. Suitable liquid media include water, aqueous solvents, serum, and mixtures thereof. Preferably, the liquid medium is mammalian serum, and more preferably, it is a mixture of human serum and bovine serum.

Other excipients, such as salts, buffers, proteins, polymers, carbohydrates, preservatives and reducing agents may also be added to the liquid medium.

A preferred embodiment of the present invention relates to stabilized conjugates of cTnI which are useful as control reagent compositions for immunoassays. Preferably, the cTnI conjugates are formed by conjugating a synthetic polymer, such as PEG, to the protein's pendant amine groups. Because cTnI's amine-containing lysine residues are not located in the cardiac-specific N-terminal portion of the protein, conjugation to PEG does not appreciably affect the ability of the cTnI to bind to cardiac-specific anti-cTnI antibodies.

In another embodiment, the present invention relates to a method of stabilizing individual subunits of multisubunit complexes by providing a solution of the individual subunit, adding a multifunctional crosslinking agent to activate the subunit, then simultaneously or subsequently adding a polymer to effect conjugation of the subunit to the polymer via the crosslinking agent. This method of stabilization is particularly preferred for conjugating serum proteins such as albumin to cTnT via glutaraldehyde, although it is also useful for other combinations of polymers and subunits as described herein, as well as with other multifunctional crosslinking agents.

MODES FOR CARRYING OUT THE INVENTION

The present invention relates to methods of stabilizing individual subunits of multisubunit protein complexes via conjugation to polymers. The term "stabilized" as used herein means that the conformation of the protein's subunit when suspended in a liquid medium is maintained for a longer period of time than the equivalent unconjugated or "free" subunit. Stabilization can be measured as a function of the subunit's ability to retain at least one biological activity when suspended in a liquid medium and stored for a period of time, relative to the subunit in its native state. For example, a subunit-polymer conjugate would be considered stabilized if it maintained a level of about 50% of at least one of its biological activities upon storage in a liquid medium, compared to a free subunit. "Biological activity" of a protein subunit can be any biological characteristic attributed at least in part to that particular subunit of a multisubunit complex, such as enzyme activity, ligand binding capacity, substrate recognition, antibody binding, nucleic acid binding and the like.

The hydrophobic interactions between subunits of multisubunit proteins (i.e. a protein's quaternary structure) lend stability to the complex, and also to the conformation of the individual subunits within the complex. Accordingly, isolation of a subunit from a multisubunit protein complex can cause many subunits to undergo conformational changes. For example, individual subunits of multisubunit *E. coli* enterotoxin have been shown to lose ligand binding capacity when separated from the native complex. Tsuji et al, *Microbiol. Immunol.* 39:817–819 (1995).

Since a protein's biological activity depends on its conformation, stability of a protein can be measured as a function of the protein's biological activity. For example, specific ligands such as antibodies that recognize the native conformation of a protein can be used to measure changes to that conformation.

Individual subunits of multisubunit proteins may be useful for a variety of purposes, such as for studying or exploiting the biological activities of each individual subunit in a multisubunit protein complex. For example, in immunoassays, where target specificity can be achieved only by targeting antibodies to a particular subunit of a multisubunit protein complex, the individual subunit is useful as a control reagent for the immunoassay.

Cardiac Troponin I (cTnI)

Troponin is a three-subunit complex of troponin I, T and C. The cardiac isoform of troponin I ("cTnI") is an ideal target for the study and diagnosis of acute myocardial infarction.

In one embodiment, the present invention relates to cTnI-polymer conjugates and methods for the preparation thereof. More particularly, this embodiment of the present invention involves conjugation of cTnI to polymers which act to prevent the uncomplexed cTnI subunit from losing its native conformation and thus losing its binding capacity for cTnI-specific antibodies during storage in a liquid medium.

The nucleic acid sequence of the gene which codes for cTnI and its amino acid sequence have previously been described by Armour et al. (*Gene* 131:287–292 (1993); GenBank Accession No. M64247, SEQ ID NO:1 and SEQ ID NO:2, respectively).

The term "cTnI" as used herein also intends fragments of cTnI that retain at least one epitope which is recognizable by a monoclonal or polyclonal antibody (or fragment thereof) that preferentially binds to cardiac isoforms of troponin I. Also included in the term "cTnI" are: polypeptides that have amino acid substitutions, deletions or insertions relative to the native or naturally occurring amino acid sequence of cTnI; and fusion proteins that contain all or a fragment of cTnI linked to another protein.

Cardiac Troponin T (cTnT)

Like cTnI, cTnT is also useful as a marker for the study of acute myocardial infarction. Thus, in another embodiment, the present invention relates to cTnT-polymer conjugates and methods for the preparation thereof. Similarly to cTnI, conjugation of cTnT to polymers also acts to maintain cTnT's native conformation.

The nucleic acid sequence of the gene which codes for cTnT and its amino acid sequence have previously been described by Townsend, et al., *Genomics*, 21(2): 311–316 (1994); GenBank Accession No. X74819; SEQ ID NO.s 3 and 4.

The term "cTnT" as used herein also intends fragments of cTnT that retain at least one epitope which is recognizable by a monoclonal or polyclonal antibody (or fragment thereof) that preferentially binds to cardiac isoforms of troponin T. Also included in the term "cTnT" are: polypeptides that have amino acid substitutions, deletions or insertions relative to the native or naturally occurring amino acid sequence of cTnI; and fusion proteins that contain all or a fragment of cTnT linked to another protein.

Isolating Individual Subunits

Protein subunits such as cTnI and cTnT can be isolated from their natural source in human or animal tissue, or they can be prepared using recombinant techniques. Recombinant techniques are well known in the art and involve isolation and/or synthesis of a polynucleotide encoding all or a fragment of the protein subunit and cloning into a suitable bacterial or eukaryotic expression vector. Such techniques are described in a variety of references, including but not limited to, *Molecular Cloning: A Laboratory Manual*, 2nd ed., Vol. 1–3, eds. Sambrook et al. Cold Spring Harbor Laboratory Press (1989). After insertion of the vector into a suitable host cell and expression of the desired protein subunit, the protein subunit can be isolated and purified using known techniques. (See, for example, *Scopes Protein Purification: Principles and Practice*, 2nd Ed., Springer-Verlag, N.Y. (1987))

In particular, cTnI can be isolated from heart muscle and substantially purified as described in PCT Patent Application No. WO 94/27156. Therein, a procedure is given for affinity purification of cTnI on a troponin C affinity column. Human heart is trimmed of excess fat and valves and cut into 1 cm pieces at 4° C. The resulting tissue is homogenized in one portion with 750 ml extraction buffer (75 mM Tris buffer, pH 8.0, containing 8 M urea, 15 mM mercaptoethanol and 1 mM calcium chloride) at ambient temperature. The homogenate is centrifuged for 30 minutes at 7000× g and the supernatant liquid is filtered through cheesecloth to remove particulate matter. Troponin C coupled to a solid support gel is equilibrated in extraction buffer, and the heart extract is added to the equilibrated troponin C-gel. The resulting suspension is allowed to stir for 80 minutes at ambient temperature and then centrifuged 20 minutes at 7000× g. The pelleted gel is transferred to a column with extraction buffer. The column is washed at ambient temperature with a total of 700 ml of extraction buffer and the purified troponin I is then eluted from the column with elution buffer (75 mM Tris buffer, pH 8.0, containing 8 M urea, 15 mM mercaptoethanol, and 10 mM ethylenediamine tetraacetic acid).

The cTnT subunit can be prepared as generally described above for cTnI, or it can be commercially obtained from a variety of companies such as Research Diagnostics, Inc., Flanders, N.J.; and HyTest, Turku, Finland.

Individual subunits of multisubunit protein complexes other than troponin can also be prepared as described above or by other known methods. In particular, individual subunits can be isolated from their natural source in biological samples by first separating the subunits, then using affinity chromatography with specific antibodies or other subunits of the complex.

Analyzing Individual Subunits

In the present invention, polymer conjugation is used to stabilize the conformation of individual protein subunits. Before proceeding with conjugation, it is preferable to first make sure the protein subunit preparation has the desired conformation. In particular, after isolation of individual subunits from multisubunit complexes, it is desirable to confirm that the isolation procedure did not adversely affect the conformation of the subunit. This can most easily be accomplished by determining whether the individual protein complex still has an acceptable level of the desired biological activity. For example, when the protein subunit is ultimately to be used as a control reagent in an immunoassay, antibody binding capacity should be determined. Testing the binding capacity of a protein for a particular antibody can be accomplished using known techniques. When the individual protein subunit is cTnI/cTnT, cardiac-specific cTnI/cTnT antibodies are used to determine antibody binding capacity. "Cardiac-specific anti-cTnI/cTnT antibodies" refers to antibodies that have a substantially greater binding affinity for cTnI/cTnT than for other troponins or skeletal forms of cTnI/cTnT. Such antibodies to cTnI have been previously described. See, inter alia, Katus et al., European Patent No. EP 394,819; Takahashi et al., PCT Patent Application No. WO 96/10076; Larue et al., *Clin. Chem.* 39:972–979 (1993); and Bodor et al., *Clin. Chem.* 38:2203–2214 (1992). Antibodies which are specific for cTnT have also been described. See for example, Bodor, et al., *Clinical Chemistry*, 43(3): 476–484 (1997), which describes a polyclonal goat anti-cTnT antibody (G136-C; Fortron BioScience, Morrisville, N.C.) which was developed against the N terminal amino acids 3–15 of human cTnT and which reportedly reacts <0.4% with skeletal isoforms. The N-terminal amino acid sequence is shown as follows:

Ile-Glu-Glu-Val-Val-Glu-Glu-Tyr-Glu-Glu-Glu-Glu-Gln (SEQ ID NO: 5)

In addition, Muller-Bardorff, et al. (*Clinical Chemistry*, 43(3): 458–466 (1997)) describe a monoclonal antibody pair (M7 and M11.7) which can be used in a sandwich assay for cTnT which reportedly cross reacts <0.3% with skeletal isoforms.

Polymers

Stabilization of individual protein subunits is achieved by conjugating the protein subunit to a polymer to prevent conformational changes of the protein subunit in the uncomplexed state and thus loss of its biological activity. The polymers of the present invention must have a high enough molecular weight to effectively stabilize the conformation of the protein subunit. Preferably, the molecular weight is between 100 to 200,000, more preferably between 1,000 and 40,000, and most preferably between 2,500 and 10,000.

The polymer may be already formed prior to conjugation to the protein subunit (i.e. the monomeric units comprising the polymer may already be covalently attached), or in the alternative, the polymer may be formed during conjugation by using monomeric units such as monosaccharides, amino acids, or alkyl groups (C2 to C20 substituted or unsubstituted, branched or unbranched, saturated, partially saturated or unsaturated) which are "polymerized" (covalently attached to one another) during conjugation to the protein, or directly attached to the protein in their monomeric form. In any event, the term "polymer" and "polymer-protein conjugate" as used herein is intended to cover any of the aforementioned variations.

The polymer can be naturally occurring or synthetic. Examples of naturally occurring polymers include proteins, glycopeptides, polysaccharides such as dextran and lipids. In the case of cTnI, the polymer is preferably a synthetic polymer. Examples of synthetic polymers which are suitable for use in the present invention include, but are not limited to, polyalkyl glycols (PAG) such as PEG, polyoxyethylated polyols (POP) such as polyoxyethylated glycerol (POG), polytrimethylene glycol (PTG), polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, or co-polymers of two or more different synthetic monomers.

The synthetic polymers of the present invention have the following generic structure:

$$R_1-(X-R_2)_a-R_3$$

where $R_1$ and $R_3$ are the same or different and are H, $H_3C$, OH, $R_2$ or a reactive group (as described below); where $R_2$ is a linear or branched substituted or unsubstituted alkyl group; where X is O (in which case the synthetic polymer may be a polyoxyalkylene) or X is NH(C=O) (in which case the synthetic polymer may be a polyamine), or X is absent (in which case the synthetic polymer may be a polyalkylene); and a is an integer between 1 and 1,000.

A preferred class of synthetic polymers are the polyethylene glycols given by the formula:

$$R_1O-(CH_2CH_2O)_a-R_3$$

where $R_1$, $R_3$ and a are as described above. The term "polyethylene glycol" (PEG) includes both unsubstituted ($R_1$=H and $R_3$=OH) as well as substituted polyethylene glycol.

Although hydrophilic polymers are preferred, it is also possible to use hydrophobic polymers, such as activated suberate or proprionate derivatives, or mixtures of hydrophilic or hydrophobic polymers.

Naturally occurring proteins which are preferred for conjugation to cTnT are serum proteins, such as albumin. For convenience, the naturally occurring protein used for conjugation to cTnT can actually be a heterogeneous mixture of proteins, such as one which would be found in animal sera (for example, bovine or human), or in a synthetically produced serum substitute.

Polymer Activation

In order to conjugate the protein subunit to a polymer (which is either already polymerized or in its monomeric form at the time of conjugation), the polymer may first need to be activated. "Activated" means the preliminary attachment of a reactive group onto the polymer. A polymer which has been activated, as well as a polymer which already contains at least one reactive group is referred to as being "active". Many synthetic polymers do not normally contain reactive groups which will react with a protein's pendant groups. For example, unsubstituted PEG has a hydroxyl group at each end of the linear polymer chain, one or both of which must first be activated before conjugation to a protein. To prevent the potential for cross-linking, it is desirable to activate only one of PEG's two hydroxyl termini to form a "monofunctional" substituted PEG. This can be accomplished by blocking one of the two hydroxyl groups with a methoxy group to form monomethoxypolyethylene glycol (mPEG).

Techniques for activating polymers prior to protein conjugation are known to those skilled in the art. See, for example, Greg T. Hermanson, *Bioconjugate Techniques*, p. 605–619 (1996) Academic Press. For example, activation of hydroxyl groups in PEG or MPEG as well as in other natural or synthetic polymers, can be accomplished using trichloro-s-triazine (TsT; cyanuric acid). (See, inter alia, Abuchowski et al., *J. Biol. Chem.* 252:3582–3586 (1977) and Abuchowski et al., *J. Biol. Chem.* 252:3578–3581 (1977)). Another method of activating hydroxyl groups is through formation of an amine reactive N-hydroxyl succinimidyl- (NHS) or p-nitrophenyl (Np) carbonate active ester. (See Zalipsky et al., *Biotechnol Appl. Biochem.* 15:100–114 (1992).)

Similar activation can be achieved when the hydroxyl-containing polymer is first reacted with a cyclic anhydride (succinic or glutaric anhydride) and then the formed carboxyl modified product is coupled with N-hydroxyl succinimide in the presence of carbodiimides resulting in succinimidyl succinate or glutarate type active esters. (See Abuchowski et al., *Cancer Biochem. Biophys.* 7:175–186 (1984).)

A further method for activating a polymer's hydroxyl groups is through formation of an imidazolyl carbamate intermediate by reaction with N,N'-carbonyldiimidazole (CDI). The CDI-activated polymer reacts with amine groups of protein to form a stable N-alkyl carbamate linkage identical to that formed with succinimidyl carbonate chemistry described above. (See Beauchamp et al., *Anal. Biochem.* 131:25–33 (1983).)

For additional methods on activating synthetic polymers, such as PEG, see inter alia, U.S. Pat. No. 5,349,001; U.S. Pat. No. 5,359,030; and U.S. Pat. No.5,446,090.

When the polymer to be conjugated to the protein subunit is a natural polymer such as a serum protein, it is generally preferred to activate the protein subunit by attachment of a multifunctional crosslinking agent as is more fully described in the following section.

Polymer-Protein Conjugation

After activation of the polymer (if necessary), the polymer is conjugated to the individual protein subunit. In general, polymers can be covalently attached to proteins via pendant groups in the protein chain, such as primary amino groups, carboxyl groups, aromatic rings, or thiol groups, all of which may already be present, or can be added by preliminary chemical modification of the protein or by modifying a protein's amino acid sequence, using known molecular biology methods. One of the most frequently used and convenient methods involves attachment of the polymer to the protein's free amino groups in lysine residues ($\epsilon$ amino group) or to the protein's N-terminal amino acid ($\alpha$-amino group). This approach is preferred when the protein's amino groups are located in segments of the protein which are not crucial to maintaining the desired biological activity, such as is the case with cTnI. The discussion which follows outlines two representative embodiments of the present invention. It is to be noted that the methodologies presented for cTnI are equally applicable for cTnT, and vice versa, as well as other protein subunits.

The ratio of polymer to protein to be used to carry out the conjugation depends on the characteristics (structure, size, charge, reactivity) of the polymer, as well as the characteristics (number and location of pendant groups, nature of the biological activity) of the individual subunit. It would be a matter of routine experimentation to determine the appropriate ratio by varying the ratio to optimize biological activity and conjugate stability.

A. cTnI-Polymer conjugates

There are three isoforms of troponin I: slow skeletal, fast skeletal and cardiac troponin I (herein referred to as "cTnI"). The three isoforms of troponin I in rabbits show about 40% sequence difference at the amino acid level, as described by Wilkinson and Grand *Nature*, 271:31–35 (1978). The nucleotide and amino acid sequences of human cTnI are given as SEQ ID NO: 1 and SEQ ID NO:2, respectively. cTnI also contains a cardiac-specific 31 amino acid N-terminal sequence, which is completely missing from either of the two skeletal isoforms, as shown below:

Met-Ala-Asp-Gly-Ser-Ser-Asp-Ala-Ala-Arg-Glu-Pro-Arg-Pro-Ala-Pro-Ala-Pro-Ile-Arg-Arg-Arg-Ser-Ser-Asn-Tyr-Arg-Ala-Tyr-Ala-Thr-(SEQ ID NO: 6)

Since this cardiac-specific segment contains no lysine residues, it is possible to conjugate polymers to amino groups located elsewhere on the protein without appreciably affecting the ability of the cTnI-PEG conjugate to bind to cardiac-specific anti-cTnI antibodies.

In the case of cTnI and PEG, the preferred ratio is between 1 and 20 moles of active PEG per mole of cTnI, more preferably between 6 and 16, and most preferably between 10 and 14. The resultant cTnI-PEG conjugate is considered stable if it retains at least 85% of its biological activity when stored at 4° C. for a period of about 30 days. In the case of cTnI, "biological activity" refers to the ability of cTnI to be recognized by cTnI-specific antibodies. The cTnI-PEG conjugate is preferentially stored at −20° C. to 23° C., more preferably between about 2° C. to about 8° C. The cTnI-PEG conjugate may also be lyophilized or stored under an inert gas such as argon, nitrogen, etc.

B. cTnT-Polymer Conjugates

In addition to conjugations which involve preactivation of the polymer, it is also possible to effect conjugation via a crosslinking agent. The crosslinking agent is preferably multifinctionally active and more preferably difinctionally active, which means that it contains more than one ("multi-") or two ("di-") reactive groups. The crosslinking agent can be one of the synthetic polymers described above which has been activated to contain two or more reactive groups, which can then be used as a linker to conjugate the protein subunit to another synthetic or natural polymer.

The crosslinking agent may also be a more conventional chemical crosslinking agent, including but not limited to, glutaraldehyde, formaldehyde, divinyl sulfane, carbodiimides, epoxides and imidazole. In the case of cTnT, glutaraldehyde is preferred.

Protein-Polymer Conjugate Compositions

Protein-polymer compositions can be formulated by diluting, dissolving or concentrating and rediluting the protein-polymer conjugate in a suitable liquid medium, such as water, aqueous solvents, serum, or mixtures thereof. Excipients can also be added to the liquid medium to further optimize the formulation. For example, cyclodextrin or other carbohydrates can be added to the protein-polymer conjugate to inhibit the rate of intermolecular aggregation during storage in the liquid medium.

Other optional components include, but are not limited to, casein, albumin, gelatin or other proteins. Buffers can be added to stabilize the pH of the liquid medium. Protease inhibitors such as phenyl methyl sulfonyl fluoride, leupeptin, pepstatin may also be included. Preservatives such as Amphotericin B, cycloheximide, chloramphenicol, bacitracin, gentamycin, chloroheximide, sodium azide, trimethoprim, sulphomethaxozole may also be included. Additionally, reducing agents such as glutathione may be added.

It may also be desirable to sterilize the protein-polymer conjugate composition after formulation, such as by means of filtration. Filtration may be accomplished by passing the protein-polymer conjugate composition through a suitable size control device, such as a filter, molecular sieves, resins, hollow fibers, and spiral cartridge exclusions. Preferably, a 0.2 micron aseptic filter is used.

Preferably, the liquid medium is mammalian serum, more preferably a mixture of bovine and human serum, which has been filter sterilized, and which also contains carbohydrates, and antimicrobial agents. For a description of such a "modified" human serum, see U.S. Pat. No. 5,556,788. The sera used in the examples which follow were modified.

EXAMPLES

Example I

Conjugation of cTnI to PEG cTnI from Scripps Laboratories (La Jolla, Calif.) was dissolved in water at 4° C. to a concentration of 1 mg/ml. To 50 µl of this cTnI solution, an equal volume of conjugation buffer (0.1 M sodium phosphate, pH=7.5) was added, and the resultant mixture was kept on ice. Meanwhile, the activated polymer solution was prepared by dissolving 5 mg methoxypolyethylene glycol p-nitrophenyl carbonate (mPEG-ONp, avg. MW=5,000) in 1 ml of ice-cold conjugation buffer. 42 µl of activated polymer solution (200 fold molar excess) were added to the buffered cTnI solution, and the mixture was incubated for 18 hours at 4° C. with slow end-to-end mixing. The cTnI-PEG conjugate thus formed was frozen and stored at −20° C. until use.

Example II

Stability of cTnI-PEG Conjugates

Figure 1:
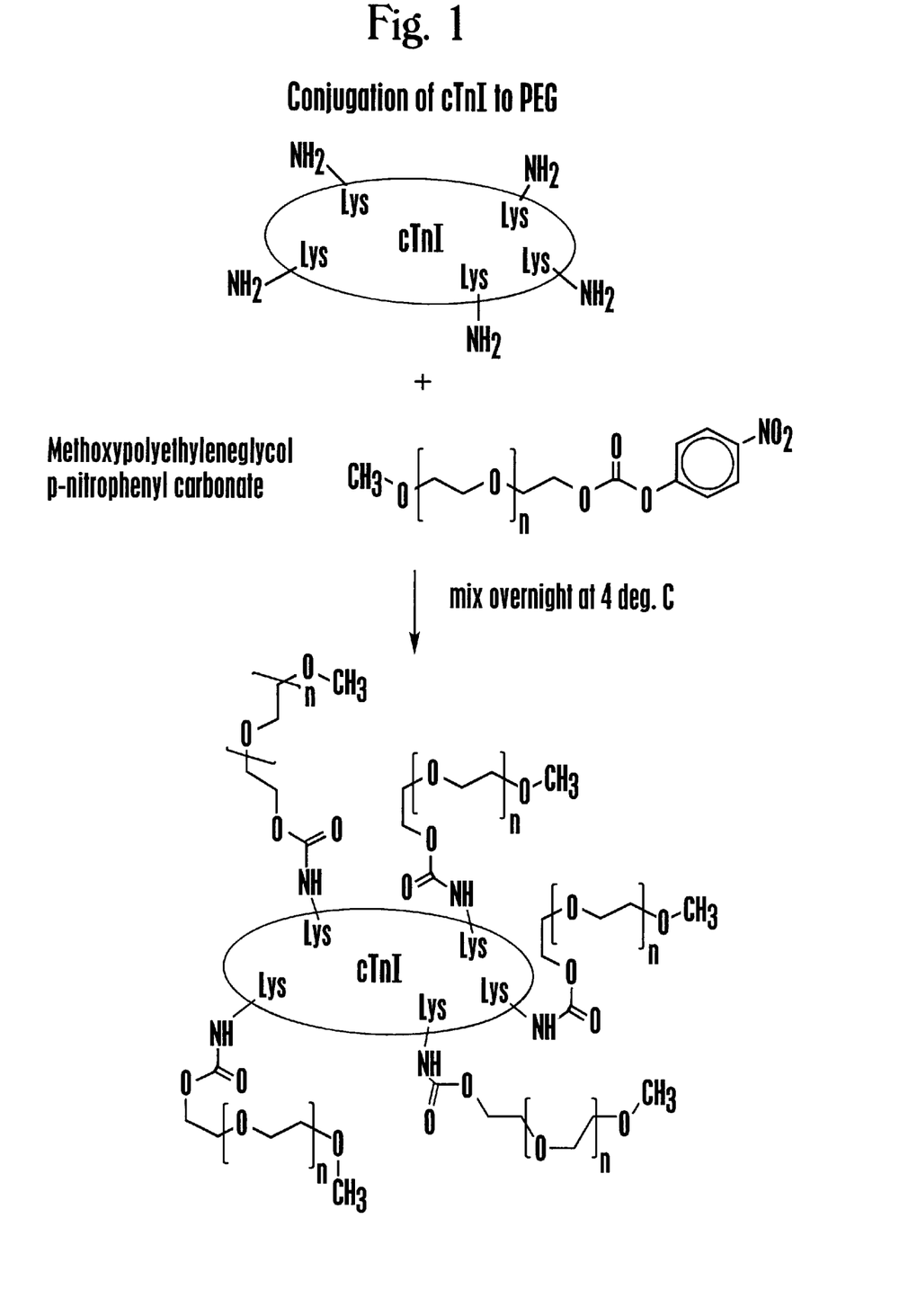
FIG. 1 is a flow diagram which shows the activation of PEG and coupling to cTnI.
Figure 2A:
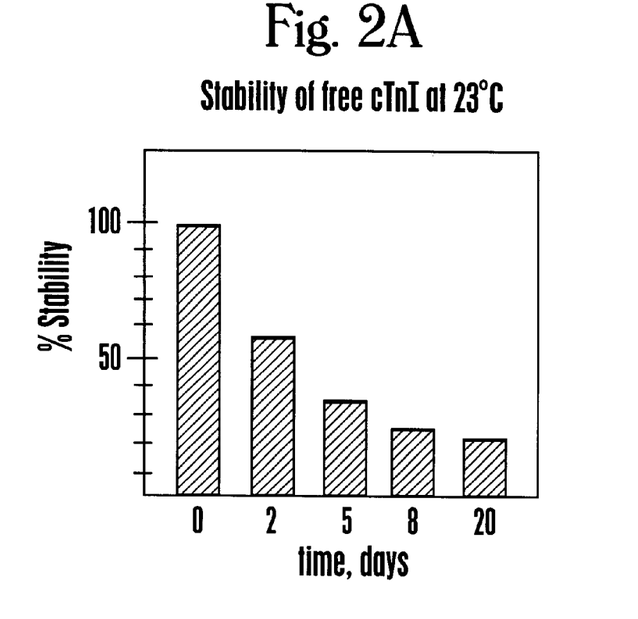
FIGS. 2A and 2B are bar graphs which show the stability of free cTnI and cTnI-PEG conjugates, respectively, at 23° C.
Figure 2B:
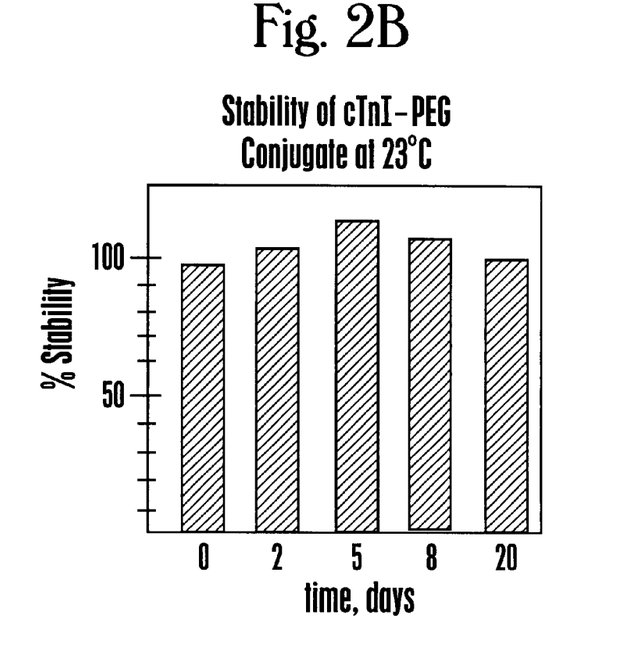
Figure 3A:
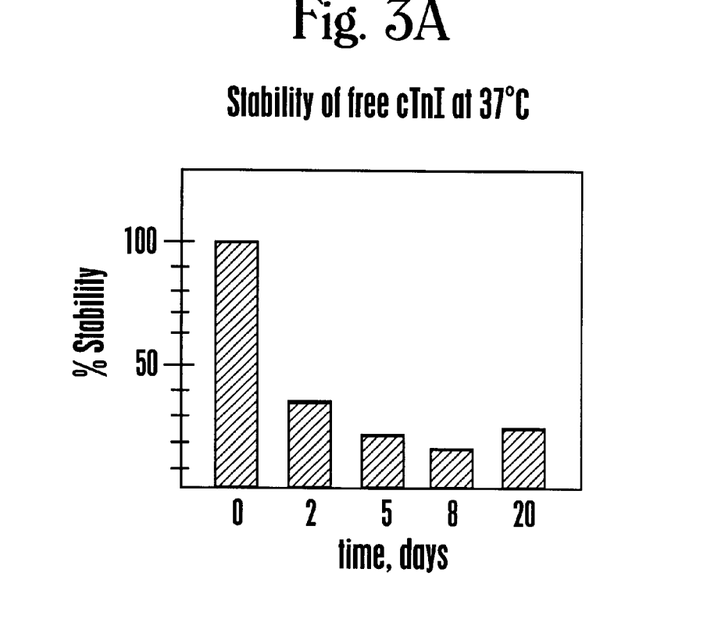
FIGS. 3A and 3B are bar graphs which show the stability of free cTnI and cTnI-PEG conjugates, respectively, at 37° C.
Figure 3B:
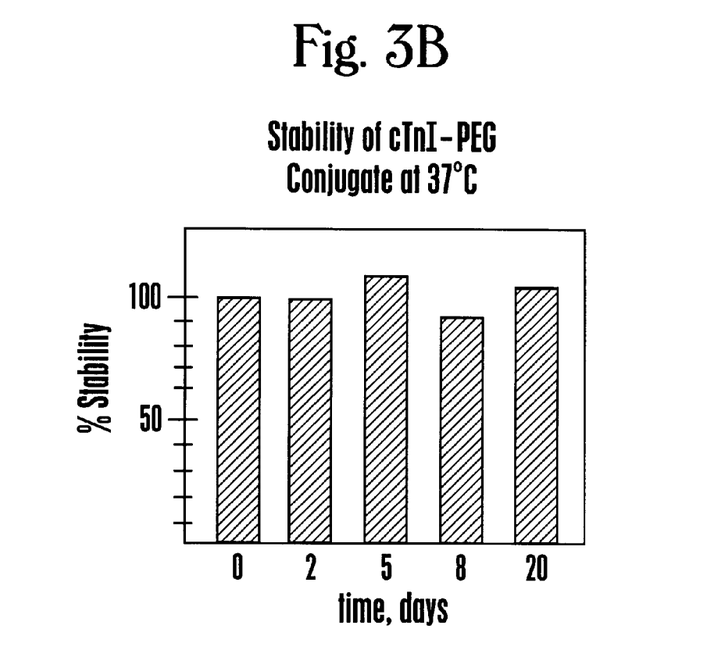
Figure 4A:
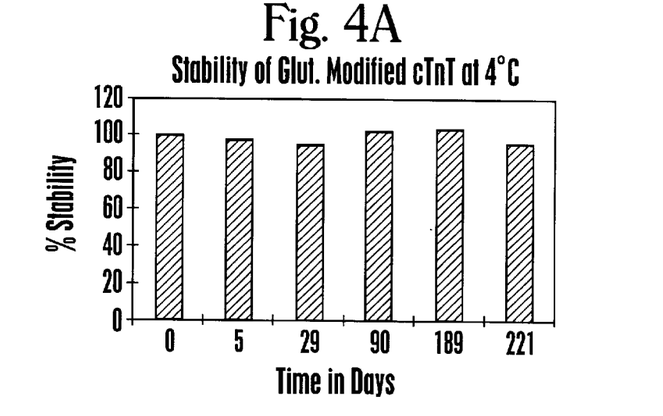
FIGS. 4A, 4B and 4C are bar graphs which show the stability of protein conjugated cTnT during storage at 4° C. or 23° C. (4A and 4B, respectively) compared to unconjugated cTnT (4C).
Figure 4B:
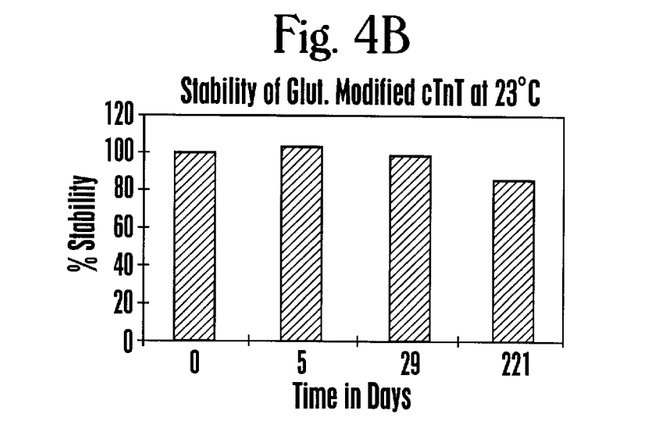
Figure 4C:
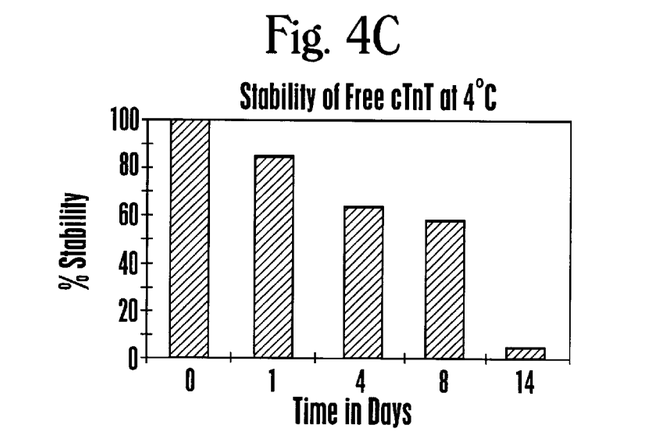

The stability of the cTnI-PEG conjugates prepared according to Example I was compared to that of unconjugated cTnI. Both the conjugated and unconjugated cTnI preparations were diluted in a liquid medium of 50% human and 50% bovine serum, and stored at various temperatures. At the indicated times, samples were removed and analyzed as described in Example III. The results are shown in FIGS. 2 and 3 as a percentage of the concentration of cTnI at a given time compared to the initial concentration (100%). The results depicted in FIG. 2 indicate that, while unconjugated cTnI stored at 23° C. for 20 days retains only about 20% of its initial antibody binding capacity, the cTnI-PEG conjugate retains essentially 100% activity when stored under the same conditions. Similar results are obtained when the unconjugated cTnI and the cTnI-PEG conjugates are stored at 37° C. as depicted in FIG. 3. Storage at 4° C. of unconjugated cTnI typically results in the loss of at least 25% of its original antibody binding activity, while the cTnI-PEG conjugate retains 100% of its activity.

Example III

Measuring Antibody Binding Capacity

Antibody binding capacity is measured using either of the two commercially available assays for the quantitative determination of cTnI levels in serum and plasma according to the manufacturer's specifications. These assays are: the Stratus® cardiac Troponin-I fluorometric enzyme inmnunoassay (Baxter Diagnostics Inc./Dade International Inc., Miami, Fla.); and the OPUS® Troponin I assay (Behring Diagnostics Inc., Westwood, Mass.).

Example IV

Conjugation of cTnT to Serum Proteins

Glutarldehyde was added to a 400 mg/mL solution of cTnT from human heart tissue (HyTest, Turku, Finland) to a concentration of 0.1%. After mixing well and refrigerating, the glutarldehyde activated cTnT was diluted 1:10 in either human serum or bovine serum. It is hypothesized that albumin, being the most prevalent protein which is present in the serum, is conjugated to the cTnT via the glutaraldehyde.

Example V

Stability of cTnT-Serum Protein Conjugates

Stability studies were performed as described above for cTnI, and the results are shown in FIGS. 4A–C. As depicted, the serum conjugated cTnT is stable for more then 6 months at either 4° C. or 23° C.

Modifications of the above-described modes for carrying out the invention that are obvious to persons of skill in the field of protein chemistry are intended to be within the scope of the following claims. All publications, patents, and patent applications cited in this specification are incorporated herein by reference as if each such publication, patent or patent application were specifically and individually indicated to be incorporated herein by reference.

We claim:

1. A stabilized individual subunit-polymer conjugate composition comprising:
   a) a polymer;
   b) an individual subunit of a multisubunit protein complex selected from cardiac troponin I (cTnI) and cardiac troponin T (cTnT); and
   c) a liquid medium,
      wherein the polymer is conjugated to the individual subunit to provide a stabilized individual subunit-polymer complex.

2. The composition according to claim 1, wherein the liquid medium is mammalian serum.

3. The composition according to claim 1, wherein the liquid medium is a mixture of human serum and bovine serum.

4. The composition of claim 1, wherein the individual subunit is cardiac Troponin I and the polymer is polyethylene glycol.

5. The composition according to claim 1, wherein the stabilized individual subunit-polymer conjugate is stable for more than 6 months at a temperature of 23° C. in said liquid medium.

6. A covalent protein-polymer conjugate in a liquid medium, wherein the protein is unconjugated cTnI and the polymer is polyethylene glycol.

7. A covalent protein-polymer conjugate in a liquid medium, wherein the protein is unconjugated cTnT and the polymer is a serum protein.

* * * * *

```
                         SEQUENCE LISTING

<160> NUMBER OF SEQ ID NOS: 6

<210> SEQ ID NO 1
<211> LENGTH: 633
<212> TYPE: DNA
<213> ORGANISM: homo sapien
<220> FEATURE:
<221> NAME/KEY: CDS
<222> LOCATION: (1)...(633)

<400> SEQUENCE: 1 atg gcg gat ggg agc agc gat gcg gct agg gaa cct cgc cct gca cca       48
Met Ala Asp Gly Ser Ser Asp Ala Ala Arg Glu Pro Arg Pro Ala Pro
 1               5                  10                  15 gcc cca atc aga cgc cgc tcc tcc aac tac cgc gct tat gcc acg gag       96
Ala Pro Ile Arg Arg Arg Ser Ser Asn Tyr Arg Ala Tyr Ala Thr Glu
            20                  25                  30 ccg cac gcc aag aaa aaa tct aag atc tcc gcc tcg aga aaa ttg cag      144
Pro His Ala Lys Lys Lys Ser Lys Ile Ser Ala Ser Arg Lys Leu Gln
        35                  40                  45
```

-continued

| | |
|---|---|
| ctg aag act ctg ctg ctg cag att gca aag caa gag ctg gag cga gag<br>Leu Lys Thr Leu Leu Leu Gln Ile Ala Lys Gln Glu Leu Glu Arg Glu<br>    50                          55                    60 | 192 |
| gcg gag gag cgg cgc gga gag aag ggg cgc gct ctg agc acc cgc tgc<br>Ala Glu Glu Arg Arg Gly Glu Lys Gly Arg Ala Leu Ser Thr Arg Cys<br>65                        70                        75                  80 | 240 |
| cag ccg ctg gag ttg gcc ggg ctg ggc ttc gcg gag ctg cag gac ttg<br>Gln Pro Leu Glu Leu Ala Gly Leu Gly Phe Ala Glu Leu Gln Asp Leu<br>                    85                        90                        95 | 288 |
| tgc cga cag ctc cac gcc cgt gtg gac aag gtg gat gaa gag aga tac<br>Cys Arg Gln Leu His Ala Arg Val Asp Lys Val Asp Glu Glu Arg Tyr<br>                100                    105                    110 | 336 |
| gac ata gag gca aaa gtc acc aag aac atc acg gag att gca gat ctg<br>Asp Ile Glu Ala Lys Val Thr Lys Asn Ile Thr Glu Ile Ala Asp Leu<br>                115                    120                    125 | 384 |
| act cag aag atc ttt gac ctt cga ggc aag ttt aag cgg ccc acc ctg<br>Thr Gln Lys Ile Phe Asp Leu Arg Gly Lys Phe Lys Arg Pro Thr Leu<br>130                        135                    140 | 432 |
| cgg aga gtg agg atc tct gca gat gcc atg atg cag gcg ctg ctg ggg<br>Arg Arg Val Arg Ile Ser Ala Asp Ala Met Met Gln Ala Leu Leu Gly<br>145                        150                    155                160 | 480 |
| gcc cgg gct aag gag tcc ctg gac ctg cgg gcc cac ctc aag cag gtg<br>Ala Arg Ala Lys Glu Ser Leu Asp Leu Arg Ala His Leu Lys Gln Val<br>                165                    170                    175 | 528 |
| aag aag gag gac acc gag aag gaa aac cgg gag gtg gga gac tgg cgc<br>Lys Lys Glu Asp Thr Glu Lys Glu Asn Arg Glu Val Gly Asp Trp Arg<br>              180                    185                    190 | 576 |
| aag aac atc gat gca ctg agt gga atg gag ggc cgc aag aaa aag ttt<br>Lys Asn Ile Asp Ala Leu Ser Gly Met Glu Gly Arg Lys Lys Lys Phe<br>                195                    200                    205 | 624 |
| gag agc tga<br>Glu Ser *<br>    210 | 633 |

<210> SEQ ID NO 2
<211> LENGTH: 210
<212> TYPE: PRT
<213> ORGANISM: homo sapien

<400> SEQUENCE: 2

Met Ala Asp Gly Ser Ser Asp Ala Ala Arg Glu Pro Arg Pro Ala Pro
1                  5                        10                        15

Ala Pro Ile Arg Arg Arg Ser Ser Asn Tyr Arg Ala Tyr Ala Thr Glu
                20                        25                        30

Pro His Ala Lys Lys Lys Ser Lys Ile Ser Ala Ser Arg Lys Leu Gln
                35                        40                        45

Leu Lys Thr Leu Leu Leu Gln Ile Ala Lys Gln Glu Leu Glu Arg Glu
    50                          55                    60

Ala Glu Glu Arg Arg Gly Glu Lys Gly Arg Ala Leu Ser Thr Arg Cys
65                        70                        75                  80

Gln Pro Leu Glu Leu Ala Gly Leu Gly Phe Ala Glu Leu Gln Asp Leu
                    85                        90                        95

Cys Arg Gln Leu His Ala Arg Val Asp Lys Val Asp Glu Glu Arg Tyr
                100                    105                    110

Asp Ile Glu Ala Lys Val Thr Lys Asn Ile Thr Glu Ile Ala Asp Leu
                115                    120                    125

Thr Gln Lys Ile Phe Asp Leu Arg Gly Lys Phe Lys Arg Pro Thr Leu
130                        135                    140

```
Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
            165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
            195                 200                 205

Glu Ser
    210

<210> SEQ ID NO 3
<211> LENGTH: 867
<212> TYPE: DNA
<213> ORGANISM: homo sapien
<220> FEATURE:
<221> NAME/KEY: CDS
<222> LOCATION: (1)...(867)

<400> SEQUENCE: 3 atg tct gac ata gaa gag gtg gtg gaa gag tac gag gag gag gag cag      48
Met Ser Asp Ile Glu Glu Val Val Glu Glu Tyr Glu Glu Glu Glu Gln
1               5                   10                  15 gaa gaa gca gct gtt gaa gag cag gag gag gca gcg gaa gag gat gct      96
Glu Glu Ala Ala Val Glu Glu Gln Glu Glu Ala Ala Glu Glu Asp Ala
            20                  25                  30 gaa gca gag gct gag acc gag gag acc agg gca gaa gaa gat gaa gaa     144
Glu Ala Glu Ala Glu Thr Glu Glu Thr Arg Ala Glu Glu Asp Glu Glu
        35                  40                  45 gaa gag gaa gca aag gag gct gaa gat ggc cca atg gag gag tcc aaa     192
Glu Glu Glu Ala Lys Glu Ala Glu Asp Gly Pro Met Glu Glu Ser Lys
    50                  55                  60 cca aag ccc agg tcg ttc atg ccc aac ttg gtg cct ccc aag atc ccc     240
Pro Lys Pro Arg Ser Phe Met Pro Asn Leu Val Pro Pro Lys Ile Pro
65                  70                  75                  80 gat gga gag aga gtg gac ttt gat gac atc cac cgg aag cgc atg gag     288
Asp Gly Glu Arg Val Asp Phe Asp Asp Ile His Arg Lys Arg Met Glu
                85                  90                  95 aag gac ctg aat gag ttg cag gcg ctg att gag gct cac ttt gag aac     336
Lys Asp Leu Asn Glu Leu Gln Ala Leu Ile Glu Ala His Phe Glu Asn
            100                 105                 110 agg aag aaa gag gag gag gag ctc gtt tct ctc aaa gac agg atc gag     384
Arg Lys Lys Glu Glu Glu Glu Leu Val Ser Leu Lys Asp Arg Ile Glu
        115                 120                 125 aga cgt cgg gca gag cgg gcc gag cag cag cgc atc cgg aat gag cgg     432
Arg Arg Arg Ala Glu Arg Ala Glu Gln Gln Arg Ile Arg Asn Glu Arg
    130                 135                 140 gag aag gag cgg cag aac cgc ctg gct gaa gag agg gct cga cga gag     480
Glu Lys Glu Arg Gln Asn Arg Leu Ala Glu Glu Arg Ala Arg Arg Glu
145                 150                 155                 160 gag gag gag aac agg agg aag gct gag gat gag gcc cgg aag aag aag     528
Glu Glu Glu Asn Arg Arg Lys Ala Glu Asp Glu Ala Arg Lys Lys Lys
                165                 170                 175 gct ttg tcc aac atg atg cat ttt ggg ggt tac atc cag aag cag gcc     576
Ala Leu Ser Asn Met Met His Phe Gly Gly Tyr Ile Gln Lys Gln Ala
            180                 185                 190 cag aca gag cgg aaa agt ggg aag agg cag act gag cgg gaa aag aag     624
Gln Thr Glu Arg Lys Ser Gly Lys Arg Gln Thr Glu Arg Glu Lys Lys
        195                 200                 205 aag aag att ctg gct gag agg agg aag gtg ctg gcc att gac cac ctg     672
```

```
                                                                                720
aat gaa gat cag ctg agg gag aag gcc aag gag ctg tgg cag agc atc
Asn Glu Asp Gln Leu Arg Glu Lys Ala Lys Glu Leu Trp Gln Ser Ile
225                 230                 235                 240

768
tat aac ttg gag gca gag aag ttc gac ctg cag gag aag ttc aag cag
Tyr Asn Leu Glu Ala Glu Lys Phe Asp Leu Gln Glu Lys Phe Lys Gln
                245                 250                 255

816
cag aaa tat gag atc aat gtt ctc cga aac agg atc aac gat aac cag
Gln Lys Tyr Glu Ile Asn Val Leu Arg Asn Arg Ile Asn Asp Asn Gln
            260                 265                 270

864
aaa gtc tcc aag acc cgc ggg aag gct aaa gtc acc ggg cgc tgg aaa
Lys Val Ser Lys Thr Arg Gly Lys Ala Lys Val Thr Gly Arg Trp Lys
        275                 280                 285

867
tag
 *
```

<210> SEQ ID NO 4
<211> LENGTH: 288
<212> TYPE: PRT
<213> ORGANISM: homo sapien

<400> SEQUENCE: 4

```
Met Ser Asp Ile Glu Glu Val Val Glu Glu Tyr Glu Glu Glu Glu Gln
 1               5                  10                  15

Glu Glu Ala Ala Val Glu Glu Gln Glu Glu Ala Ala Glu Glu Asp Ala
             20                  25                  30

Glu Ala Glu Ala Glu Thr Glu Glu Thr Arg Ala Glu Glu Asp Glu Glu
         35                  40                  45

Glu Glu Glu Ala Lys Glu Ala Glu Asp Gly Pro Met Glu Glu Ser Lys
     50                  55                  60

Pro Lys Pro Arg Ser Phe Met Pro Asn Leu Val Pro Pro Lys Ile Pro
 65                  70                  75                  80

Asp Gly Glu Arg Val Asp Phe Asp Asp Ile His Arg Lys Arg Met Glu
                 85                  90                  95

Lys Asp Leu Asn Glu Leu Gln Ala Leu Ile Glu Ala His Phe Glu Asn
            100                 105                 110

Arg Lys Lys Glu Glu Glu Glu Leu Val Ser Leu Lys Asp Arg Ile Glu
        115                 120                 125

Arg Arg Arg Ala Glu Arg Ala Glu Gln Gln Arg Ile Arg Asn Glu Arg
    130                 135                 140

Glu Lys Glu Arg Gln Asn Arg Leu Ala Glu Glu Arg Ala Arg Arg Glu
145                 150                 155                 160

Glu Glu Glu Asn Arg Arg Lys Ala Glu Asp Glu Ala Arg Lys Lys Lys
                165                 170                 175

Ala Leu Ser Asn Met Met His Phe Gly Gly Tyr Ile Gln Lys Gln Ala
            180                 185                 190

Gln Thr Glu Arg Lys Ser Gly Lys Arg Gln Thr Glu Arg Glu Lys Lys
        195                 200                 205

Lys Lys Ile Leu Ala Glu Arg Arg Lys Val Leu Ala Ile Asp His Leu
    210                 215                 220

Asn Glu Asp Gln Leu Arg Glu Lys Ala Lys Glu Leu Trp Gln Ser Ile
225                 230                 235                 240

Tyr Asn Leu Glu Ala Glu Lys Phe Asp Leu Gln Glu Lys Phe Lys Gln
                245                 250                 255

Gln Lys Tyr Glu Ile Asn Val Leu Arg Asn Arg Ile Asn Asp Asn Gln
```

```
                    260                 265                 270
Lys Val Ser Lys Thr Arg Gly Lys Ala Lys Val Thr Gly Arg Trp Lys
            275                 280                 285

<210> SEQ ID NO 5
<211> LENGTH: 13
<212> TYPE: PRT
<213> ORGANISM: homo sapien

<400> SEQUENCE: 5

Ile Glu Glu Val Val Glu Glu Tyr Glu Glu Glu Glu Gln
 1               5                  10

<210> SEQ ID NO 6
<211> LENGTH: 31
<212> TYPE: PRT
<213> ORGANISM: homo sapien

<400> SEQUENCE: 6

Met Ala Asp Gly Ser Ser Asp Ala Ala Arg Glu Pro Arg Pro Ala Pro
 1               5                  10                  15

Ala Pro Ile Arg Arg Arg Ser Ser Asn Tyr Arg Ala Tyr Ala Thr
            20                  25                  30
```